(12) United States Patent
Takahashi et al.

(10) Patent No.: US 10,213,076 B2
(45) Date of Patent: Feb. 26, 2019

(54) PARTICLE COLLECTING APPARATUS AND PARTICLE COLLECTING METHOD

(71) Applicant: TOKYO ELECTRON LIMITED, Tokyo (JP)

(72) Inventors: Nobuhiro Takahashi, Nirasaki (JP); Keiko Hada, Nirasaki (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 766 days.

(21) Appl. No.: 13/626,997

(22) Filed: Sep. 26, 2012

(65) Prior Publication Data

US 2013/0074281 A1 Mar. 28, 2013

(30) Foreign Application Priority Data

Sep. 28, 2011 (JP) .................................. 2011-213229

(51) Int. Cl.
| | |
|---|---|
| *A47L 9/00* | (2006.01) |
| *B08B 5/02* | (2006.01) |
| *B08B 5/04* | (2006.01) |
| *G01N 15/06* | (2006.01) |
| *G01N 15/00* | (2006.01) |
| *G01N 1/22* | (2006.01) |

(52) U.S. Cl.
CPC .................. *A47L 9/00* (2013.01); *B08B 5/02* (2013.01); *B08B 5/04* (2013.01); *G01N 1/2202* (2013.01); *G01N 15/06* (2013.01); *G01N 2001/2223* (2013.01); *G01N 2015/0046* (2013.01)

(58) Field of Classification Search
CPC ..... A47L 9/00; A47L 5/14; B08B 5/02; B08B 5/04; B08B 3/02; B08B 7/028; G01N 15/06; G01N 1/2202; G01N 2001/2223; G01N 2015/0046
USPC ........................................................... 15/381
See application file for complete search history.

(56) References Cited

U.S. PATENT DOCUMENTS 4,718,975 A * 1/1988 Bowling ........... H01L 21/67766
118/50.1
5,879,314 A * 3/1999 Peterson ............ A61B 17/2251
601/2

(Continued)

FOREIGN PATENT DOCUMENTS

| JP | 61140823 A * 6/1986 |
|---|---|
| JP | 61140823 A * 6/1986 |

(Continued)

OTHER PUBLICATIONS

Machine translation of JP2000-005715 dated Jan. 2000.*

(Continued)

*Primary Examiner* — Douglas Lee
(74) *Attorney, Agent, or Firm* — Cantor Colburn LLP (57) ABSTRACT

A particle collecting apparatus is provided with a case, an ultrasonic generator, a gas supplying unit, a suction unit and a seal member. The case has one end, and defines a space at the one end. The ultrasonic generator is provided in the case, and generates ultrasonic waves towards the opening defined by the one end of the case. The gas supplying unit supplies gas to the space. The suction unit exhausts the space. The seal member has elasticity, and is provided at the one end so as to surround the opening.

5 Claims, 7 Drawing Sheets

(56) References Cited

U.S. PATENT DOCUMENTS

| | | | |
|---|---|---|---|
| 6,223,455 B1* | 5/2001 | Chickering, III | B01J 2/04 34/578 |
| 6,821,320 B1* | 11/2004 | Miyazaki | B03C 3/011 96/17 |
| 2002/0096195 A1 | 7/2002 | Harvey et al. | |
| 2005/0075620 A1* | 4/2005 | Iger | A61M 37/0092 604/500 |
| 2007/0285631 A1* | 12/2007 | Stavenga | G03F 7/70916 355/30 |
| 2008/0223364 A1* | 9/2008 | Hickey | A61M 11/02 128/203.12 |
| 2009/0005727 A1* | 1/2009 | Hood | A61M 37/0092 604/65 |

FOREIGN PATENT DOCUMENTS

| | | | |
|---|---|---|---|
| JP | 62092642 | | 6/1987 |
| JP | 62110544 | | 7/1987 |
| JP | 62110544 U | * | 7/1987 |
| JP | 05057257 | | 3/1993 |
| JP | 10180209 | | 7/1998 |
| JP | 2000005715 A | * | 1/2000 |
| JP | 2000005715 A | * | 1/2000 |
| JP | 2000062197 | | 2/2000 |
| JP | 2001237283 | | 8/2001 |
| JP | 2007152222 | | 6/2007 |
| JP | 2008178778 A | * | 8/2008 |
| JP | 2008178778 A | * | 8/2008 |

OTHER PUBLICATIONS

Machine translation of JP2008-178778 dated Aug. 2008.*
Machine translation of JP2000-05715 dated Jan. 2000.*
Abstract of JP61-140823 dated Jun. 1986.*
Machine translation of JP2008-178778 dated Aug. 2008 (Year: 2008).*
Machine translation of JP2000-05715 dated Jan. 2000 (Year: 2000).*
Abstract of JP61-140823 dated Jun. 1986 (Year: 1986).*

* cited by examiner

PARTICLE COLLECTING APPARATUS AND PARTICLE COLLECTING METHOD

TECHNICAL FIELD

Various aspects of the present invention relates to a particle collecting apparatus and a particle collecting method.

BACKGROUND

Patent Document 1 discloses an apparatus that collects particles deposited on a surface of a solid. The apparatus described in Patent Document 1 irradiates ultrasonic waves to a solid to separate particles from the surface of the solid, and electrically charges the particles by an ion generator to electrically collect the charged particles.

Patent Document 2 discloses an apparatus that collects particles deposited on a surface of a substrate. The apparatus described in Patent Document 2 sprays a gas to the surface of the substrate, and sucks the particles separated from the surface of the substrate.

PRIOR ARTS

Patent Document

Patent Document 1: Japanese Patent Application Laid-Open No. H10-180209
Patent Document 2: U.S. Patent Application Publication No. 2002/0096195

SUMMARY

Problems to be Solved by the Invention

In the particle collecting apparatuses as described in Patent Documents 1 and 2, particles may not be collected efficiently in some cases because particles separated from the surface of a target object such as a solid or a substrate may be scattered in the space.

Accordingly, an apparatus and a method capable of collecting particles more efficiently are required in this technical field.

Means for Solving the Problems

The particle collecting apparatus according to one aspect of the present invention is provided with a case, an ultrasonic generator, a gas supplying unit, a suction unit and a seal member. The case has one end, and defines a space that is opened at the one end. The ultrasonic generator is provided in the case, and generates ultrasonic waves towards an opening defined by the one end of the case. The gas supplying unit supplies gas to the space. The suction unit exhausts the space. The seal member has elasticity, and is provided at the one end of the case so as to surround the opening.

The particle collecting apparatus may be used in a state where the seal member is in contact with a target object. Accordingly, the particle collecting apparatus collects particles in a state where the space defined by the case is closed. Further, in the particle collecting apparatus, ultrasonic waves are irradiated to a target object, and as a result, particles are separated from the target object. Accordingly, it is possible to separate particles from a target object while preventing deterioration of the target object. Then, gas is supplied to the closed space, and the separated particles are sucked along with the gas by the suction unit. As a result, the particle collecting apparatus makes it possible to separate particles efficiently from a target object and to suppress particles from scattering out of the space defined by the case. Furthermore, the particles may be suppressed from re-adhering to the target object by the gas supply and suction. Therefore, the particle collecting apparatus makes it possible to collect particles efficiently. Further, it is also possible to suppress the contamination of the target object by supplying inert gas along with ultrasonic waves without using any foreign substances such as water or chemical liquids. Further, by the gas supply and suction, it is possible to clean the inside of the case, and maintain the above-described space clean.

In an embodiment, the gas supplying unit may include a supplying pipe having one end that defines a gas injection hole connected to the space. The gas injection hole may be extended in an inclined direction with respect to the opening or a plane in parallel with the opening.

In an embodiment, the suction unit may include a suction pipe having one end that defines a suction hole connected to the space. The suction hole may be extended in an inclined direction with respect to the opening or a plane in parallel with the opening. Further, in an embodiment, the suction hole may be provided in symmetrically with respect to the gas injection hole. According to this embodiment, the gas and particles are sucked in the reflected direction of the gas and particles from a target object. Therefore, it is possible to achieve even higher efficiency of collecting particles.

In an embodiment, the gas supplying unit may include a supplying pipe having one end that defines a gas injection hole connected to the space. The gas injection hole may be extended in parallel with a plane including the opening.

In an embodiment, the suction unit may include a suction pipe having one end that defines a suction hole connected to the space. The suction hole may be extended in parallel with a plane including the opening. Further, in an embodiment, the suction hole may be provided symmetrically with respect to the gas injection hole. According to this embodiment, the gas and particles are sucked in the injected direction of the gas. Therefore, it is possible to achieve even higher efficiency of collecting particles.

In an embodiment, the suction unit may include a suction pipe having one end. The one end of the suction pipe may be extended through the space towards the opening, and may also be extended along with the inner side of the case so as to insert the space between the gas injection hole and the one end of the suction pipe. According to this embodiment, particles are sucked in the opening, that is, near the target object. Therefore, it is possible to achieve even higher efficiency of collecting particles.

In an embodiment, the suction unit may include a particle counter. According to this embodiment, it is possible to count the number of the collected particles with high efficiency.

The particle collecting method according to another aspect of the present invention includes providing a seal member at one end of a case so as to surround an opening defined by the one end, bringing the seal member into contact with a target object, thereby defining a closed space between the target object and the case, irradiating ultrasonic waves to the target object, supplying gas into the space, and exhausting the space. According to this particle collecting method, it is possible to efficiently separate particles from a target object. Further, particles are suppressed from scattering out of the space. Therefore, it is possible to achieve higher efficiency of collecting particles.

Effects of the Invention

As described above, according to various aspects and various embodiments of the present invention, an apparatus and a method for collecting particles more efficiently are provided.

DETAILED DESCRIPTION

Hereinafter, the detailed description will be provided regarding to various embodiments in reference with drawings. In each drawing, the same or the corresponding part has the same reference numeral.

Figure 1:
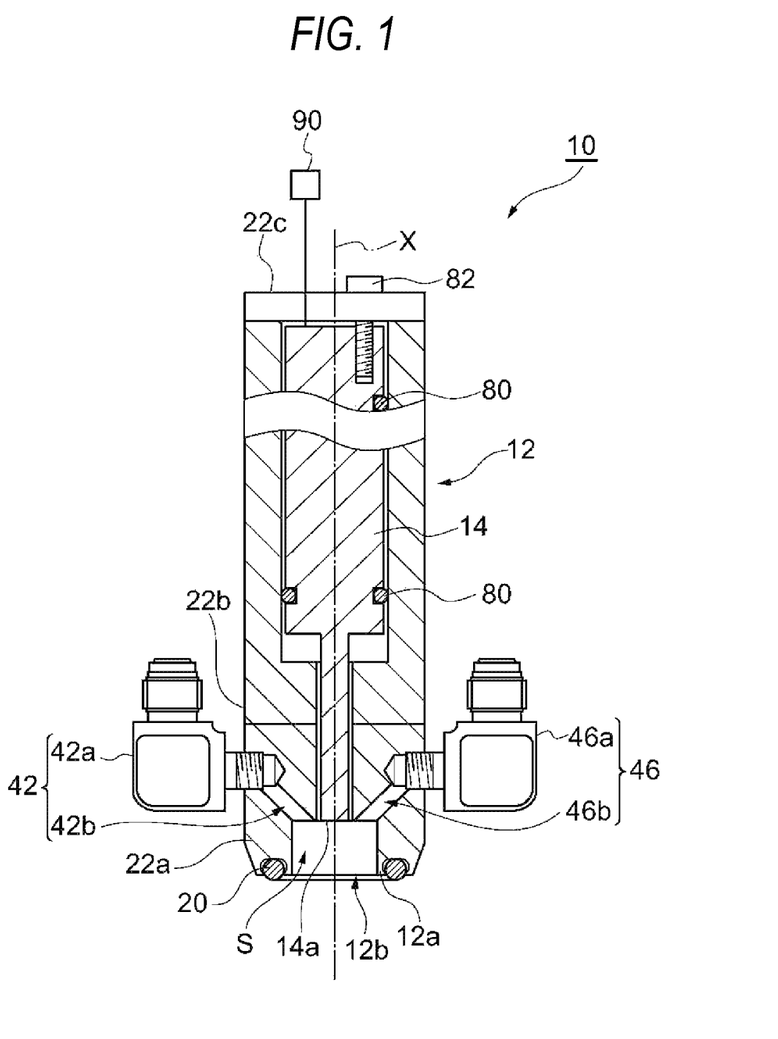
FIG. 1 is a plan view illustrating a particle collecting apparatus according to an embodiment, a portion of which is cut off.
Figure 2:
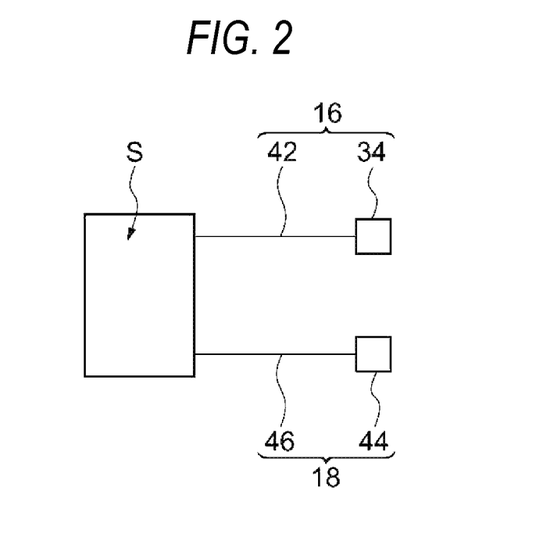
FIG. 2 is a diagram illustrating a piping system of the particle collecting apparatus according to an embodiment.

FIG. 1 is a plan view illustrating a particle collecting apparatus according to an embodiment, a portion of which is cut off. FIG. 2 is a diagram illustrating a piping system of the particle collecting apparatus according to an embodiment. The particle collecting apparatus 10 as illustrated in FIGS. 1 and 2 is provided with a case 12, an ultrasonic generator 14, a gas supplying unit 16, a suction unit 18 and a seal member 20.

The case 12 has an approximately cylindrical shape, and is extended along with its axial line X as a central axial line. The case 12 is opened at one end, and has a detachable one end 12a (head). Further, the one end 12a may be formed integrally with the case 12. The one end 12a defining an opening 12b exists at a front end of the case 12 in the direction of the axial line X. The portion of the front end side in the direction of the axial line X, that is, the portion including the one end 12a defines a space S that is opened at the one end 12a. The depth of the space S is preferably 1 mm to 15 mm, and more preferably 1 mm to 10 mm.

The case 12 includes a first portion 22a and a second portion 22b. The first portion 22a provides the one end 12a as described above, and also defines the space S. The case 12 may be made of metal materials such as aluminum or stainless steel. Or, the case 12 may be made by coating a metal on a resin substrate. The case 12, especially the surface of the portion defining the space S may be mirror-finished. In order to obtain a mirror-finished surface, a polishing method such as, for example, an electrolytic polishing may be used. By mirror-finishing the surface of the portion defining the space S, it is possible to suppress particles from being attached to the surface. An annular groove is formed on the front end surface of the first portion 22a of the case 12. An annular seal member 20 having elasticity is inserted into the groove. The seal member 20 may be, for example, an O-ring made of fluorine-based resin.

The second portion 22b is fixed at the rear side of the first portion 22a, for example, by fixing members (not illustrated) such as screws. The rear end of the second portion 22b is closed by a cover 22c which is attachable to and detachable from the second portion 22b. The second portion 22b accommodates the ultrasonic generator (horn) 14 in the interior space. In an embodiment, the ultrasonic generator 14 has an approximately cylindrical shape, and is extended along with its axial line X. The ultrasonic generator 14 may be provided with an ultrasonic transducer in the main body, and the main body of the ultrasonic generator 14 may be made of, for example, stainless steel. An O-ring 80 is interposed between the inner side of the second portion 22b of the case 12 and the ultrasonic generator 14. The case 12 is sealed at the rear end side by the O-ring 80. The front end surface (horn surface) 14a of the ultrasonic generator 14 passes through the first portion 22a to be exposed to the space S, and is interposed in the space S to face the opening 12b. The ultrasonic generator 14 irradiates ultrasonic waves, which is generated from the front end surface 14a, via the opening 12b towards a target object surface (a surface including particles). The frequency of the ultrasonic waves generated by the ultrasonic generator 14 is preferably, for example, 15 KHz to 1000 KHz, and more preferably 15 KHz to 200 KHz. In an embodiment, the ultrasonic generator 14 is connected to a control unit 90. The control unit 90 supplies electric signals to the ultrasonic generator 14. These electric signals supply electric power to the ultrasonic generator 14 to generate ultrasonic waves, and also control the power and frequency of the ultrasonic waves to be generated.

In an embodiment, the ultrasonic generator 14 is detachable from the case 12. The ultrasonic generator 14 can be taken out, for example, by removing the cover 22c from the second portion 22b. Further, in an embodiment, the ultrasonic generator 14 is movable along with the axial line X by a moving mechanism 82. The moving mechanism 82 may be constituted with a feed screw which is rotatably attached to the cover 22c and penetrates the cover 22c to screw into the ultrasonic generator 14. Further, the case 12 may be provided with a means (not illustrated) for restricting the rotation of the center of the axial line X of the ultrasonic generator 14. According to this constitution, it is possible to regulate the location of the front end surface 14a of the ultrasonic generator 14 in the direction of the axial line X by rotating the feed screw. That is, it is possible to regulate the distance between the front end surface 14a and the target object surface. In an embodiment, the moving mechanism 82 may be constituted with a ball screw. In addition, the distance between the front end surface 14a of the ultrasonic generator 14 and the front end of the case 12, that is, the opening 12a, is in a range of preferably 1 mm to 15 mm, and more preferably 1 mm to 10 mm. That is, it is preferred that the front end surface 14a is as close to the target object surface as possible. Specifically, the location of the front end surface 14a may be a location that generates standing waves efficiently when transmitting ultrasonic waves.

Next, reference is made to FIG. 2. The gas supplying unit 16 supplies gas to the space S. The flow rate of the gas supplied from the gas supplying unit 16 to the space S is preferably, for example, 0.1 L/min to 500 L/min, and more preferably 5 L/min to 200 L/min. In an embodiment, as illustrated in FIG. 2, the gas supplying unit 16 includes a gas supplying system 34 and a supplying pipe 42.

The gas supplying system 34 supplies a flow-controlled gas to the supplying pipe 42. The gas supplied by the gas supplying system 34 is an inert gas such as, for example, $N_2$ gas or Ar gas. The supplying pipe 42 defines a gas supplying line that supplies gas from the gas supplying system 34 to the space S.

Referring to FIG. 1, the supplying pipe 42 includes a conduit 42a in an embodiment. The conduit 42a is mounted on the case 12, and connected to a gas injection hole 42b formed in the case 12. That is, in an embodiment, the case 12 constitutes a part of the supplying pipe 42, that is, one end of the supplying pipe 42.

In an embodiment, the gas injection hole 42b is extended in an inclined direction with respect to a plane including the opening 12b or a plane in parallel with the plane. That is, as illustrated in FIG. 2, the gas injection hole 42b is extended in a direction which intersects with the axial line X. From the gas injection hole 42b, gas is injected in an inclined direction with respect to the opening 12b.

Reference is made to FIG. 2 again. The suction unit 18 exhausts the space S. The suction amount of the suction unit 18 is preferably, for example, 0.1 L/min to 500 L/min, and more preferably 5 L/min to 200 L/min. In an embodiment, the suction unit 18 includes a particle counter 44 and a suction pipe 46 as illustrated in FIG. 2.

The particle counter 44 has a function to exhaust the space S as well as a function to count the number of the particles sucked. The particle counter 44 is connected to the suction pipe 46.

Referring to FIG. 1, the suction pipe 46 includes a conduit 46a in an embodiment. The conduit 46a is mounted on the case 12, and connected to a suction hole 46b formed in the case 12. That is, the case 12 constitutes a part of the suction pipe 46, that is, one end of the suction pipe 46 in an embodiment.

In an embodiment, the suction hole 46b is extended in an inclined direction with respect to a plane including the opening 12b or a plane in parallel with the plane. Further, the suction hole 46b may be provided symmetrically with respect to the gas injection hole 42b. That is, as illustrated in FIG. 1, the suction hole 46b may be provided approximately in axial symmetry with the gas injection hole 42b with respect to the axial line X.

The particle collecting apparatus 10, as described above, makes it possible to count the number of particles attached on a target object. The target object is, for example, a component in a chamber of a semiconductor manufacturing apparatus. The particle collecting apparatus 10 is used in a state where the seal member 20 is brought into contact with the target object. In this state, the space S is closed by the case 12, the seal member 20 and the target object. Then, the ultrasonic waves generated from the front end surface 14a of the ultrasonic generator 14 are irradiated towards the target object. As a result, particles are separated from the target object. Accordingly, it is possible to separate particles from the target object while suppressing deterioration of the target object. Further, the separated particles are sucked from the suction hole 46b to the particle counter 44 together with the gas supplied from the gas injection hole 42b to the space S. Therefore, according to the particle collecting apparatus 10, it is possible to collect particles efficiently in the closed space S, and count the number of the collected particles as well. Furthermore, in the particle collecting apparatus 10, the particles may be suppressed from being re-attached onto the target object by gas supply and suction. In addition, it is also possible to suppress the target object from being contaminated by supplying inert gas together with ultrasonic waves without foreign substance such as water and chemical liquids. Further, owing to the gas supply and suction, it is possible to clean the inside of the case 12, and maintain the space S clean as well.

Further, in an embodiment in which the suction hole 46b is provided in a direction where the gas injected from the gas injection hole 42b is reflected from the target object, it is possible to collect particles more efficiently without damaging the target object.

Hereinafter, the present invention will be described in detail with reference to examples, but the present invention is not limited to these examples. In the particle collecting apparatus of the example, the diameter of the opening 12b and the space S is set to 22 mm, and the distance from the opening 12b to the front end surface 14a of the ultrasonic generator 14 is set to 15 mm. As the particle counter 44, μLPC-0710, manufactured by Particle Measuring Systems Inc. (U.S.A.), is used. In addition, the suction amount of the suction unit 18 is set to 28.3 L/min by generating ultrasonic waves having a frequency of 22 KHz from the ultrasonic generator 14.

Particles are collected from a target object using the particle collecting apparatus of the present example. The target object is a ceramic member which is used as a component part in a semiconductor manufacturing apparatus, and is obtained by cleaning in pure water for 5 minutes using ultrasonic waves having a frequency of 40 KHz.

Further, as a comparative example, particles are collected from the same target object as in the example using Surface Particle Detector QIII+ manufactured by Pentagon Technologies (U.S.A.). Likewise, in the comparative example, the suction amount of gas is set to 28.3 L/min.

The number of particles collected in the example and in the comparative example is shown in Table 1. The particle diameter and the number of particles shown in Table 1 are resulted from the output of the measurement result of the particle counter in the example and the output of the measurement result of Surface Particle Detector QIII+ in the comparative example. As seen from Table 1, it is confirmed that the particle collecting apparatus of the example can collect particles more efficiently than the apparatus of the comparative example in the measurable range of particle diameter greater than 0.3 μm. Further, in the particle collecting apparatus of the example, it is possible to collect particles having a particle diameter of 0.3 μm or less.

TABLE 1

| | Particle diameter (μm) | | | | | | | |
|---|---|---|---|---|---|---|---|---|
| | 0.07 | 0.1 | 0.15 | 0.2 | 0.3 | 0.5 | 0.7 | 1 |
| Number of Particles (Example) | 6 | 2 | 3 | 16 | 33 | 35 | 25 | 14 |
| Number of Particles (Comparative Example) | | | | | 4 | 3 | 1 | 0 |

Figure 3:
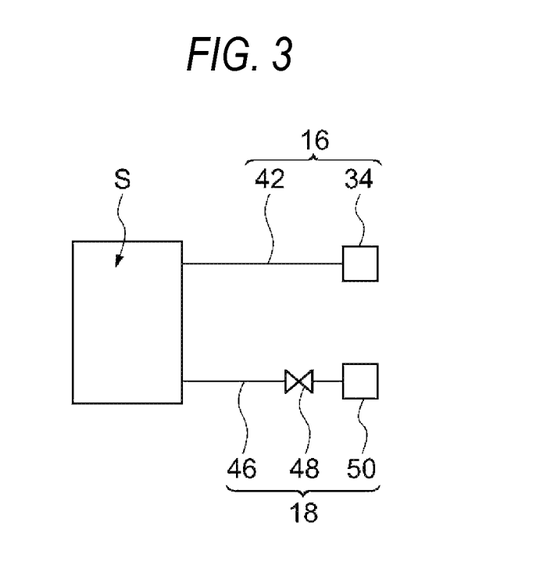
FIG. 3 is a diagram illustrating a piping system of a particle collecting apparatus according to another embodiment.

Hereinafter, description will be made with respect to another embodiment. FIG. 3 is a diagram illustrating a piping system of a particle collecting apparatus according to another embodiment. As illustrated in FIG. 3, a exhauster 50 may be used in an embodiment instead of the particle counter 44 of the particle collecting apparatus 10. The exhauster 50 may be connected via a valve 48 to the suction pipe 46. The particle collecting apparatus 10 including the exhauster 50 is used, for example, for cleaning the target object, and can clean the surface of the target object without damaging the target object.

Figure 4:
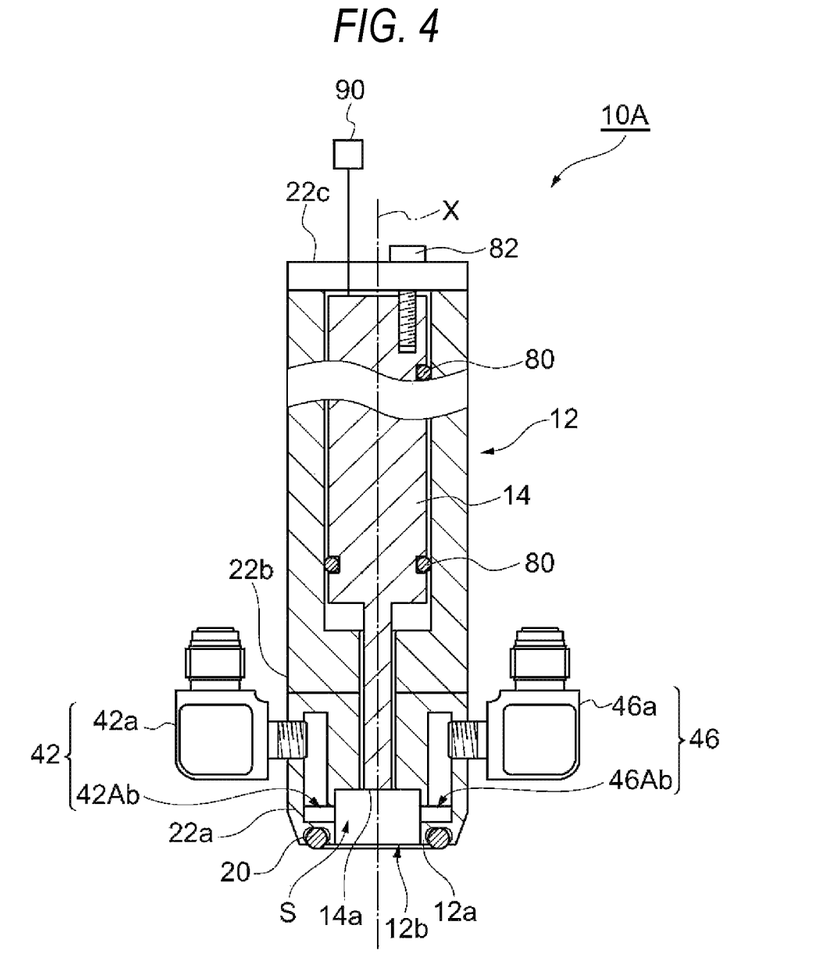
FIG. 4 is a plan view illustrating a particle collecting apparatus according to still another embodiment, a portion of which is cut off.

Hereinafter, description will be made with respect to still another embodiment. FIG. 4 is a plan view illustrating a particle collecting apparatus according to still another embodiment, a portion of which is cut off. In the particle collecting apparatus 10A as illustrated in FIG. 4, a gas injection hole 42Ab and a suction hole 46Ab are formed in the case 12, instead of the gas injection hole 42b and the suction hole 46b, respectively.

The gas injection hole 42Ab is formed in the first portion 22a of the case 12 so as to be extended in parallel with a plane including the opening 12b, that is, in an orthogonal direction to the axial line X. The suction hole 46Ab is formed in the first portion 22a of the case 12 so as to be extended in an orthogonal direction to the axial line X. Further, the suction hole 46Ab may be provided symmetrically with the gas injection hole 42Ab in an embodiment, that is, in axial symmetry with the gas injection hole 42Ab with respect to the axial line X.

The particle collecting apparatus 10A can also collect particles with high efficiency. Further, according to an embodiment in which the suction hole 46Ab is provided in an injection direction of gas from the gas injection hole 42Ab, it is possible to collect particles more efficiently without damaging the target object.

Figure 5:
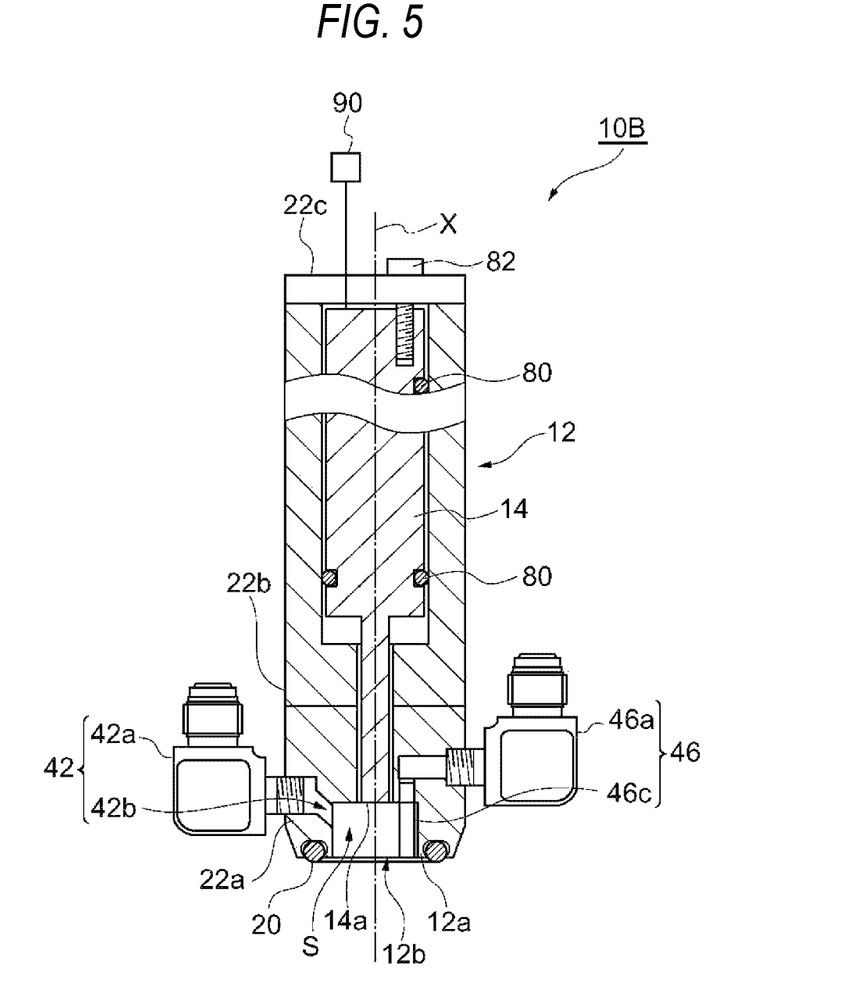
FIG. 5 is a plan view illustrating a particle collecting apparatus according to yet another embodiment, a portion of which is cut off.

Next, reference is made to FIG. 5. FIG. 5 is a plan view illustrating a particle collecting apparatus according to yet another embodiment, a portion of which is cut off. In the particle collecting apparatus 10B as illustrated in FIG. 5, the suction pipe 46 includes the conduit 46a and a conduit 46c.

The conduit 46c is connected to the conduit 46a. The conduit 46c constitutes one end of the suction pipe 46. The conduit 46c is extended through the space S towards the opening 12b. Further, the conduit 46c is extended along with the inner side of the first portion 22a of the case 12 defining the space S such that the space S is inserted between the injection hole 42b and the conduit 46c in an orthogonal direction to the axial line X. The conduit 46c is also extended in parallel with the axial line X.

In the particle collecting apparatus 10B, since the conduit 46c, that is, the front end of the suction pipe 46 can stand close to the opening 12b, it is possible to suck particles from the front end of the suction pipe 46. According to the particle collecting apparatus 10B, it is therefore possible to collect particles with high efficiency without damaging the target object.

Figure 6:
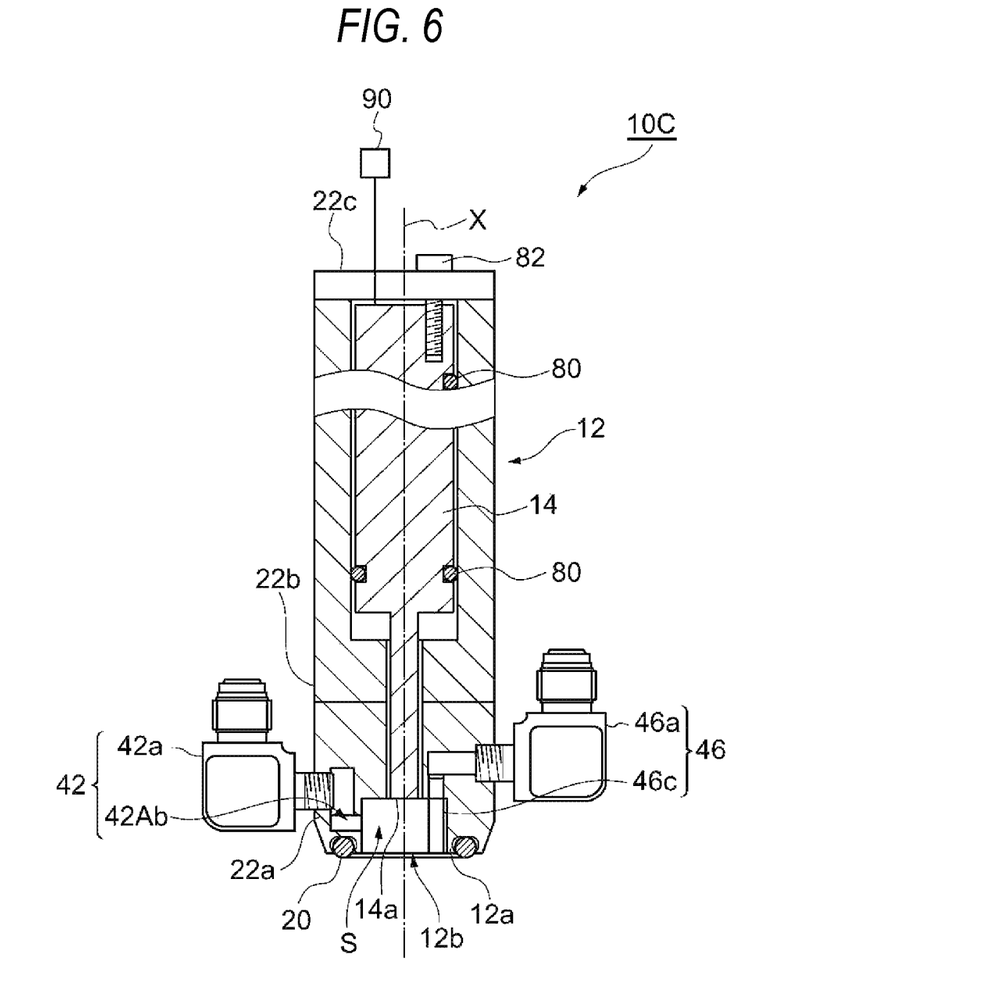
FIG. 6 is a plan view illustrating a particle collecting apparatus according to still yet another embodiment, a portion of which is cut off.

Next, reference is made to FIG. 6. FIG. 6 is a plan view illustrating a particle collecting apparatus according to still yet another embodiment, a portion of which is cut off. In the particle collecting apparatus 10C as illustrated in FIG. 6, the constitution of the suction pipe 46 is the same as that of the suction pipe 46 in the particle collecting apparatus 10B. Here, in the particle collecting apparatus 10B, the gas injection hole 42b is extended in an inclined direction with respect to the axial line X, as in the case of the gas injection hole 42b of the particle collecting apparatus 10 as illustrated in FIG. 1. Meanwhile, in the particle collecting apparatus 10C, the gas injection hole 42Ab is extended in an orthogonal direction to the axial line, as in the case of the particle injection hole 42Ab of the particle collecting apparatus 10A as illustrated in FIG. 4.

Figure 7:
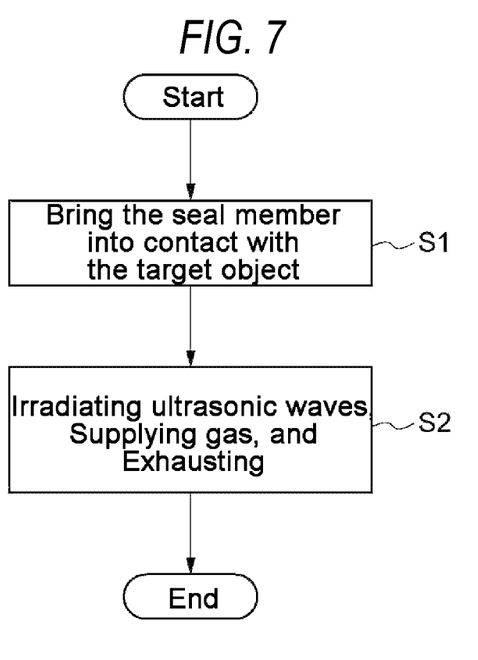
FIG. 7 is a flow chart illustrating a particle collecting method according to an embodiment.

Hereinafter, a particle collecting method according to an embodiment will be described. FIG. 7 is a flow diagram illustrating a particle collecting method according to an embodiment. Although the particle collecting method is described with respect to the case of using the particle collecting apparatus as illustrated in FIG. 1, the particle collecting method as illustrated in FIG. 7 can be performed using a particle collecting apparatus of any embodiments as described above.

Figure 8:
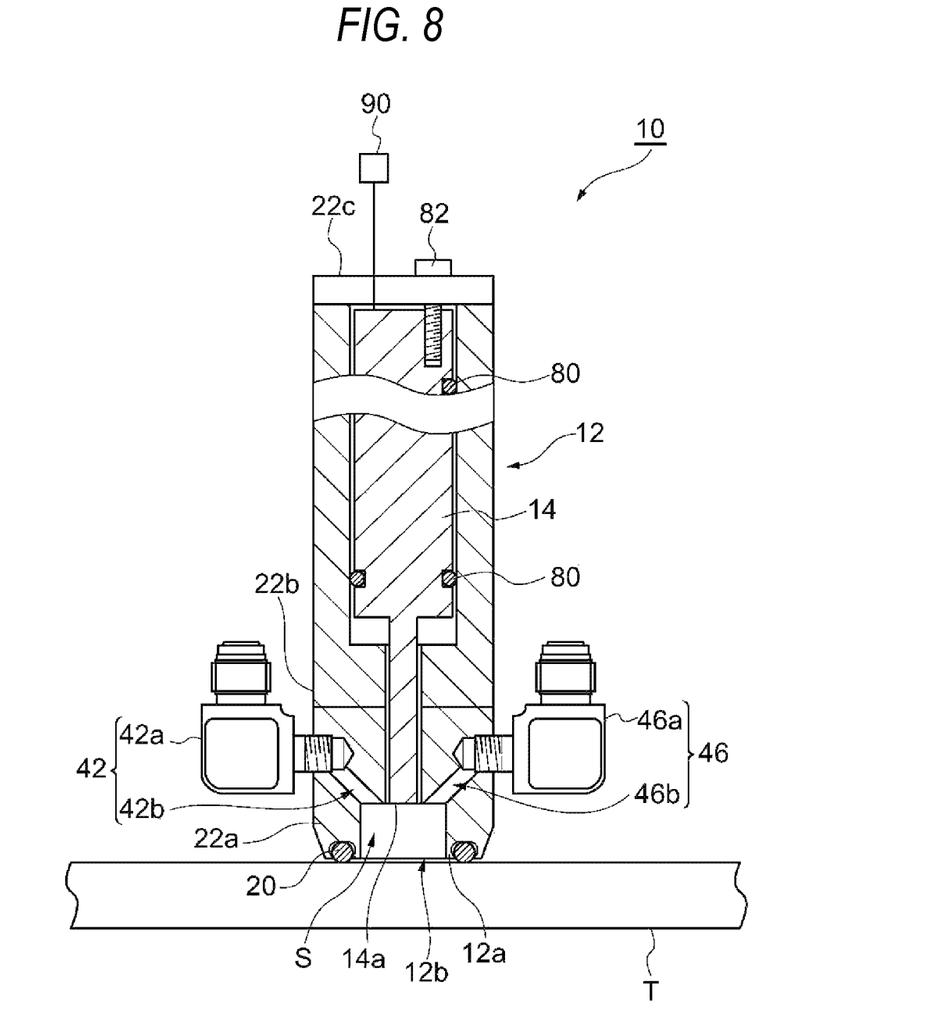
FIG. 8 is a diagram illustrating a state where a seal member of the particle collecting apparatus according to an embodiment is brought into contact with a target object.

In the particle collecting method according to an embodiment as illustrated in FIG. 7, the seal member 20 is first brought into contact with a target object at Step S1. FIG. 8 is a diagram illustrating a state where a seal member of a particle collecting apparatus according to an embodiment is brought into contact with a target object. As illustrated in FIG. 8, when the seal member 20 is in contact with a target object T, the space S defined by the case 12 is closed by the surface of the target object T. That is, the closed space S is defined between the case 12 and the target object T.

Subsequently, at Step S2, ultrasonic waves are irradiated from the ultrasonic generator 14 towards the target object T, gas is supplied from the gas supplying unit 16 to the space S, and the space S is exhausted by the suction unit 18. As a result, particles are separated from the target object T, and the separated particles are sucked along with the gas supplied from the gas supplying unit 16 by the suction unit 18. Further, particles are suppressed from scattering out of the space S. According to the particle collecting method, it is therefore possible to collect particles with high efficiency without damaging the target object.

In the particle collecting apparatuses of the various embodiments as described above, the location of the ultrasonic generator 14 can be adjusted in a direction of the axial line X inside the case 12. Accordingly, by adjusting the distance between the target object and the front end surface 14a of the ultrasonic generator 14 depending on the material of the target object or the particle diameter or the shape of the particle to be collected, it is possible to enhance the collecting efficiency of particles without damaging the target object.

Further, in the particle collecting apparatuses of the various embodiments as described above, the ultrasonic generator 14 is detachable from the case 12. Accordingly, the ultrasonic generator 14 may be combined with a case having a front end shape following the surface shape of the target object. As a result, it is possible to collect particles, for example, even from a target object having a curved surface without damaging the target object. In addition, it is possible to separate the case 12 and then clean the case 12.

Although various embodiments have been described, various modifications may be made without being limited to the above-described embodiments. For example, it is possible to use any formation of the constitution including the supplying pipe and the suction pipe in the above-described embodiments.

EXPLANATION OF REFERENCE NUMERALS AND SYMBOLS

10 . . . Particle collecting apparatus, 12 . . . Case, 12a . . . One end, 12b . . . Opening, 14 . . . Ultrasonic generator, 14a . . . Front end surface, 16 . . . Gas supplying unit, 18 . . . Suction unit, 20 . . . Seal member, 42 . . . Supplying pipe, 42b, 42Ab . . . Gas injection hole, 44 . . . Particle counter, 46 . . . Suction pipe, 46b, 46Ab . . . Suction hole, S . . . Space.

What is claimed is:

1. A particle collecting apparatus comprising:

a case having one end configured to define a space that is opened at the one end;

an ultrasonic generator configured to irradiate ultrasonic waves generated from a front end surface thereof towards a target object via an opening defined by the one end of the case, and separate particles from the target object;

a gas supplying unit including a supplying pipe configured to be connected to the space in order to supply gas to the space;

a suction unit including a suction pipe configured to be connected to the space in order to collect the particles separated from the target object along with the gas supplied from the gas supplying unit; and a seal member having elasticity, and provided at the one end so as to surround the opening, wherein the case includes a first portion providing the one end of the case, and a second portion fixed at a rear side of the first portion and configured to accommodate the ultrasonic generator therein, a rear end of the second portion being closed by a cover which is attachable to and detachable from the second portion, the supplying pipe has one end that defines a gas injection hole connected to the space and formed in the first portion of the case so as to be extended in an inclined direction with respect to the opening or a plane in parallel with the opening, the suction pipe has one end that defines a suction hole connected to the space and formed in the first portion of the case so as to be extended in an inclined direction with respect to the opening or a plane in parallel with the opening, and the suction hole is provided in axial symmetry with the gas injection hole with respect to an axial line of the case, and wherein the particle collecting apparatus further includes a moving mechanism rotatably attached to the cover, penetrating the cover to screw into the ultrasonic generator, and configured to move the ultrasonic generator along the axial line of the case in order to control a distance between the front end surface of the ultrasonic generator and the target object.

2. The particle collecting apparatus of claim 1, wherein the supplying pipe has one end that defines a gas injection hole connected to the space, and the gas injection hole is extended in parallel with a plane including the opening.

3. The particle collecting apparatus of claim 2, wherein the suction pipe has one end that defines a suction hole connected to the space, and the suction hole is extended in parallel with a plane including the opening.

4. The particle collecting apparatus of claim 1, wherein the suction unit includes a particle counter.

5. The particle collecting apparatus of claim 1, wherein the suction hole is provided in a direction where the gas injected from the gas injection hole is reflected from the target object.

* * * * *